(12) United States Patent
Munishkin et al.

(10) Patent No.: US 6,916,613 B2
(45) Date of Patent: Jul. 12, 2005

(54) COMPOSITIONS, METHODS, KITS AND APPARATUS FOR DETERMINING THE PRESENCE OR ABSENCE OF TARGET MOLECULES

(75) Inventors: Alexander Munishkin, Santa Cruz, CA (US); Abraham Grossman, Pleasantville, NY (US)

(73) Assignee: Q-RNA, Inc., New York, NY (US)

( * ) Notice: Subject to any disclaimer, the term of this patent is extended or adjusted under 35 U.S.C. 154(b) by 56 days.

(21) Appl. No.: 09/844,935

(22) Filed: Apr. 27, 2001

(65) Prior Publication Data

US 2003/0180725 A1 Sep. 25, 2003

Related U.S. Application Data

(63) Continuation of application No. 09/229,287, filed on Jan. 13, 1999, now Pat. No. 6,225,058.
(60) Provisional application No. 60/071,310, filed on Jan. 13, 1998.

(51) Int. Cl.$^7$ .......................... C12Q 1/68; C12N 15/00; C12N 15/63; C12N 1/20; C07H 21/04
(52) U.S. Cl. .................. 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1

(58) Field of Search ................. 435/6, 91.1, 91.2, 435/320.1; 536/24.3, 23.4, 22.1; 935/6; 436/518; 530/350; 195/28

(56) References Cited

U.S. PATENT DOCUMENTS 3,444,043 A  *  5/1969  Spiegelman
5,977,061 A  *  11/1999  Holy .............................. 514/7

OTHER PUBLICATIONS

Marsh, L. et al., Mutational analysis of the core and modulator sequences of the BMV RN3 subgenomic promoter, Nuceic Acids Research, vol. 16, No. 3 (1998).*

* cited by examiner

*Primary Examiner*—Jeffrey Fredman
*Assistant Examiner*—Arun Chakrabarti
(74) *Attorney, Agent, or Firm*—Stephen J. Gaudet; Anthony Janiuk

(57) ABSTRACT

The present invention is directed to methods, compositions, kits and apparatus to identify and detect the presence or absence of target analytes. The embodiments of the present invention have utility in medical diagnosis and analysis of various chemical compounds in specimens and samples, as well as the design of test kits and apparatus for implementing such methods.

10 Claims, 7 Drawing Sheets

COMPOSITIONS, METHODS, KITS AND APPARATUS FOR DETERMINING THE PRESENCE OR ABSENCE OF TARGET MOLECULES

This application is a continuation of U.S. patent application Ser. No. 09/229,287 filed Jan. 13, 1999 now U.S. Pat. No. 6,225,058 which is a continuation in part of co-pending provisional application serial No. 60/071,310, filed Jan. 13, 1998.

FIELD OF THE INVENTION

The present invention is directed to methods, compositions, kits and apparatus to identify and detect the presence or absence of target analytes. The embodiments of the present invention have utility in medical diagnosis and analysis of various chemical compounds in specimens and samples, as well as the design of test kits and apparatus for implementing such methods.

BACKGROUND OF THE INVENTION

Molecular biology advances in the last decade gave great promise for the introduction of new, sensitive technologies to identify various analytes in test specimens, including the ability to diagnose cancer, infectious agents and inherited diseases. Clinical molecular diagnostics depend almost exclusively on restriction enzyme analyses and nucleic acid hybridization (Southern and Northern blots) (Meselson and Yuan, 1968, Southern, 1975). Clinical tests based on molecular biology technology are more specific than conventional immunoassay procedures and can discriminate between genetic determinants of two closely related organisms. With their high specificity, nucleic acid procedures are very important tools of molecular pathology. However, nucleic acid procedures have limitations, the most important of which are the procedures consume time, are labor intensive and have low sensitivity (Nakamura 1993).

There exists a need to perform analytical and diagnostic assays of high sensitivity and high specificity. There exists a need for analytical methods, compositions and devices which facilitate the performance of a analytical or diagnostic procedure in less than one hour. There exists a need for analytical methods, compositions and devices which are directed to targets which are present in cells in quantities less than one to one thousand copies. There exists a need for analytical and diagnostic procedures which identify small or large organic molecules, peptides or proteins, the tertiary structure of nucleic acids or complex or simple carbohydrates.

SUMMARY OF THE INVENTION

The present invention features methods, compositions, kits, and apparatus for determining the presence or absence of a target molecule. One embodiment of the present invention is a composition. The composition comprises a first ribonucleic acid (RNA) molecule. The first RNA molecule binds a target molecule and has the following formula:

5'-A-B-C-D-E-3'.

As used above, A is a section of the RNA molecule having 10–100,000 nucleotides which section is, with another RNA sequence, E, replicated by an RNA replicase. The letter "B" denotes a section of the RNA molecule having approximately 1 to 50000 nucleotides which section, with another sequence D, binds the target molecule under binding conditions. The letter "C" denotes a section of the RNA molecule having approximately 1 to 10000 nucleotides which section is capable preventing the replication of the first molecule by the RNA replicase. The letter "D" denotes a section of the RNA molecule having approximately 1 to 50000 nucleotides which section, with another sequence B, binds the target molecule under binding conditions. The sections B and D, in combination, comprise in total at least 10 nucleotides. The first RNA molecule, with sections B and D bound to target, is acted upon by the RNA replicase to form a second RNA molecule. The second RNA molecule has the following formula:

5'-E'-X-A'-3'.

As used above, E' is the complement to E, and A' is the complement to A. The letter "X" denotes the complement of parts of the sections B, and D which may be replicated, or the letter denotes the direct bond between sections E' and A'. The second RNA molecule is replicated by the RNA replicase under replicating conditions.

Preferably, the sequences represented by the letters "A" and "E" are selected from the group of sequences consisting of MDV-I RNA, Q-beta RNA microvariant RNA, nanovariant RNA, midivariant RNA, RQ-135 and modifications of such sequences which maintain the ability of the sequences to be replicated by Q-beta replicase. Preferably, the replicase is Q-beta replicase.

Preferably, the sections B and D have a combined total of 20–5,000 nucleotides and, even more preferred, 20–50 nucleotides. Preferably, the sections B and D bind to target through non-nucleic acid base pairing interactions. Sections B and D bind to the target in the manner of naturally occurring nucleic acid which form RNA-protein complexes. Or, the B and D sections are non-naturally occurring sequences which are selected to bind the target. These non-naturally occurring sequences are selected by computer modeling, or aptamers or partial aptamers, and other nucleic acids exhibiting affinity to the target. The term "aptomer" is used in the manner of Klug, S. J. and Famulok, M. "All you wanted to know about SELEX", Molecular Biology Reports, 20:97–107 (1994) and other nucleic acids which are selected for affinity to a selected target. Aptamers are selected for a particular functionality, such as binding to small or large organic molecules, peptides or proteins, the tertiary structure of nucleic acids or complex or simple carbohydrates.

Preferably, the section B has a hybridization sequence of 1–100, and more preferred, 1–50, and most preferred, 1–5 nucleotides adjacent to the section A which form a hybridization product with a complementary hybridization sequence of section D. The nucleotides of the hybridization sequence of section D are adjacent section E. The hybridization sequences of sections B and D preferably define a loop, bulge or other single stranded structure at such times that section B and D are bound to target. In the absence of target, the hybridization sequences do not form a stable hybridization product. In the presence of the target, and the formation of a complex between sections B and D with the target, a hybridization product is formed that allows the RNA replicase to skip sections B, C and D and replicate sections A and E.

Preferably, X comprises less than five nucleotides of sections B and D, and the second molecule resembles a wild-type template.

Preferably, the section C has 1–10,000 nucleotides, and more preferred, 1–1000 nucleotides, and most preferred, 1–100 nucleotides which sequences define a stop sequence for the RNA replicase. Stop sequences comprise one or more sequences which the RNA replicase can not read through to effect replication of the sequence. These sequences include, by way of example, without limitation, a sequence of poly A, poly C, poly G, multiple initiation sites, modified nucleotides which do not allow the RNA replicase to act on the sequence, sugar linkages without nucleotides and altered phosphate or sugar linkages.

Preferably, the sections A and E comprise at least one sequence that hybridizes to a third nucleic acid. Such third nucleic acid forms a hybridization product which hybridization product can be detected by known means.

A second embodiment of the present invention features paired RNA molecules comprising a first RNA molecule. The first RNA molecule binds a target molecule and has the following formula:

5'-A-F-B-3'.

And, the second RNA binds the target and has the following formula:

5'-D-H-E-3'

As used above, A is a section of the RNA molecule having 10–100,000 nucleotides which section is, with another RNA sequence, E, replicated by an RNA replicase. The letter "B" denotes a section of the RNA molecule having approximately 1 to 50000 nucleotides which section, with another sequence D, binds the target molecule under binding conditions. The letter "D" denotes a section of the RNA molecule having approximately 1 to 50000 nucleotides which section, with another sequence B, binds the target molecule under binding conditions. The sections B and D, in combination, comprise in total at least 10 nucleotides. The letter "F" denotes a section of the RNA molecule having has a hybridization sequence of 1–10,000, and more preferred, 1–50, and most preferred, 1–5 nucleotides which form a hybridization product with a complementary hybridization sequence of section H. The letter "H" denotes a section of the RNA molecule having has a hybridization sequence of 1–10,000, and more preferred, 1–50, and most preferred, 1–5 nucleotides which form a hybridization product with a complementary hybridization sequence of section F. The hybridization sequences of sections F and H preferably define a hairpin or double stranded structure at such times that section B and D are bound to target. In the absence of target, the hybridization sequences do not form a stable hybridization product. In the presence of the target, and the formation of a complex between sections B and D with the target, a hybridization product is formed that allows the RNA replicase to skip sections B and D and replicate sections A and E to form a third RNA molecule. The third RNA molecule has the following formula:

5'-E'-X-A'-3'.

As used above, E' is the complement to E, and A' is the complement to A. The letter "X" denotes the complement of parts of the sections B, F, H and D which may be replicated, or the letter denotes the direct bond between sections E' and A'. The third RNA molecule is replicated by the RNA replicase under replicating conditions. Preferably, X comprises less than five nucleotides of the complement of sections B and D, and the third molecule resembles a wild-type template.

Preferably, the sections F and H may comprise sequences which are associated with RNA replicase templates.

A further embodiment of the present invention features a method of determining the presence or absence of a target molecule. One method comprises the steps of providing a first RNA molecule. The first RNA molecule is capable of binding to a target molecule and has the formula:

5'-A-B-C-D-E-3'.

The sections A, B, C, D and E are as previously described. The method further comprises the step of imposing binding conditions on a sample potentially containing target molecules in the presence of the first RNA molecule. In the presence of the target molecule, the first RNA molecule forms a target-first RNA molecule complex. The method further comprises the step of imposing RNA replicase reaction conditions on the sample, in the presence of an RNA replicase, to form a second RNA molecule in the presence of target. The second RNA molecule has the formula:

5'-A'-X-E'-3'.

The sections A', X and E' are as previously defined. The sample is monitored for the presence of the second RNA molecule or its complement, which presence or absence is indicative of the presence or absence of the target molecule.

A second method comprises the steps of providing paired RNA molecules comprising a first RNA molecule and a second RNA molecule. The first RNA molecule is capable of binding to a target molecule and has the formula:

5'-A-F-B-3'.

The second RNA molecule has the formula:

5'-D-H-E-3'

The sections A, B, D, E, F and H are as previously described. The method further comprises the step of imposing binding conditions on a sample potentially containing target molecules in the presence of the first RNA molecule and second RNA molecule. In the presence of the target molecule, the first RNA molecule and the second RNA molecule forms a target-first second RNA molecule complex. The method further comprises the step of imposing RNA replicase reaction conditions on the sample, in the presence of an RNA replicase, to form a third RNA molecule in the presence of target. The third RNA molecule has the formula:

5'-E'-X-A'-3'.

As used above, E' is the complement to E, and A' is the complement to A. The letter "X" denotes the complement of parts of the sections B, F, H and D which may be replicated, or the letter denotes the direct bond between sections E' and A'.

A further embodiment of the present invention comprises a kit for determining the presence or absence of a target molecule. The kit comprises a one or more reagents comprising a first RNA molecule for use with an RNA replicase. The first RNA molecule has the formula:

5'-A-B-C-D-E-3'.

In the presence of target, the first RNA molecules is capable of forming a target-first-RNA complex and in the presence of an RNA replicase, forming a second RNA molecule having the formula:

5'-A'-X-E'-3'.

The letters A, B, C. D, E, A' E' and X are as previously described. The second RNA molecule is preferably capable of being replicated by Q-beta replicase.

A second embodiment of the kit for determining the presence or absence of a target molecule features paired RNA molecules. The kit comprises a one or more reagents comprising a first RNA molecule and a second RNA molecule. The first RNA molecule has the formula:

5'-A-F-B-3'.

The second RNA molecule has the formula:

5'-D-H-E-3'

In the presence of target, the first RNA molecule and the second RNA molecule are form a target-first-second RNA complex and in the presence of an RNA replicase, forming a third RNA molecule having the formula:

5'-A'-X-E'-3'.

The letters A, B, C. D, E, ,F, H, A' E' and X are as previously described. The third RNA molecule is preferably capable of being replicated by Q-beta replicase.

An embodiment of the present invention further comprises a method of making a first RNA molecule, wherein the first RNA molecule has the formula:

5'-A-B-C-D-E-3'.

As used above, the letters A, B, C, D, and E are as previously described. The method comprises the step of combining a sample containing the target molecule with a library of RNA molecules having the formula:

5'-A-B'-C-D'-E-3'.

to form a mixture of one or more target bound RNA molecules and one or more unbound RNA molecules. The letters B' and D' represent potential sections B and D. Next, primer nucleic acid corresponding to at least one section is added to the mixture with an enzyme capable of degrading the unbound RNA molecules. Next, bound RNA molecules are released from target and amplified to form an amplification product. Next, the RNA molecules comprising the amplification product having the formula:

5'-A-B'-C-D'-E--3' are sequenced. Or, a cDNA formed and such cDNA cloned into suitable vectors.

Preferably, the steps of forming a mixture, degrading unbound RNA molecules and amplifying the bound RNA molecules are repeated.

Preferably, the sections B' and D' are randomized nucleotides. Or, in the alternative, are generated through in vitro selection.

Preferably the step of degrading the unbound RNA molecules is performed in the presence of the enzyme reverse transcriptase. Sections B and D identified in the method above can be used to make paired RNA molecule of the formula:

5'-A-F-B-3';

and,

5'-D-H-E-3'.

An embodiment of the present invention further comprises a kit for performing the above method of identifying first and second RNA molecules. The kit comprises one or more nucleic acid molecules having sections corresponding to the sections A, B', C, D', and E. Preferably, the kit comprises sections B' and E' as randomized nucleotide sequences.

As used herein the term "kit" refers to an assembly of parts, compositions and reagents with suitable packaging materials and instructions.

The present invention is further described in the following figure and examples, which illustrate features and highlight preferred embodiments and the best mode to make and use the invention.

DETAILED DESCRIPTION

Figure 1:
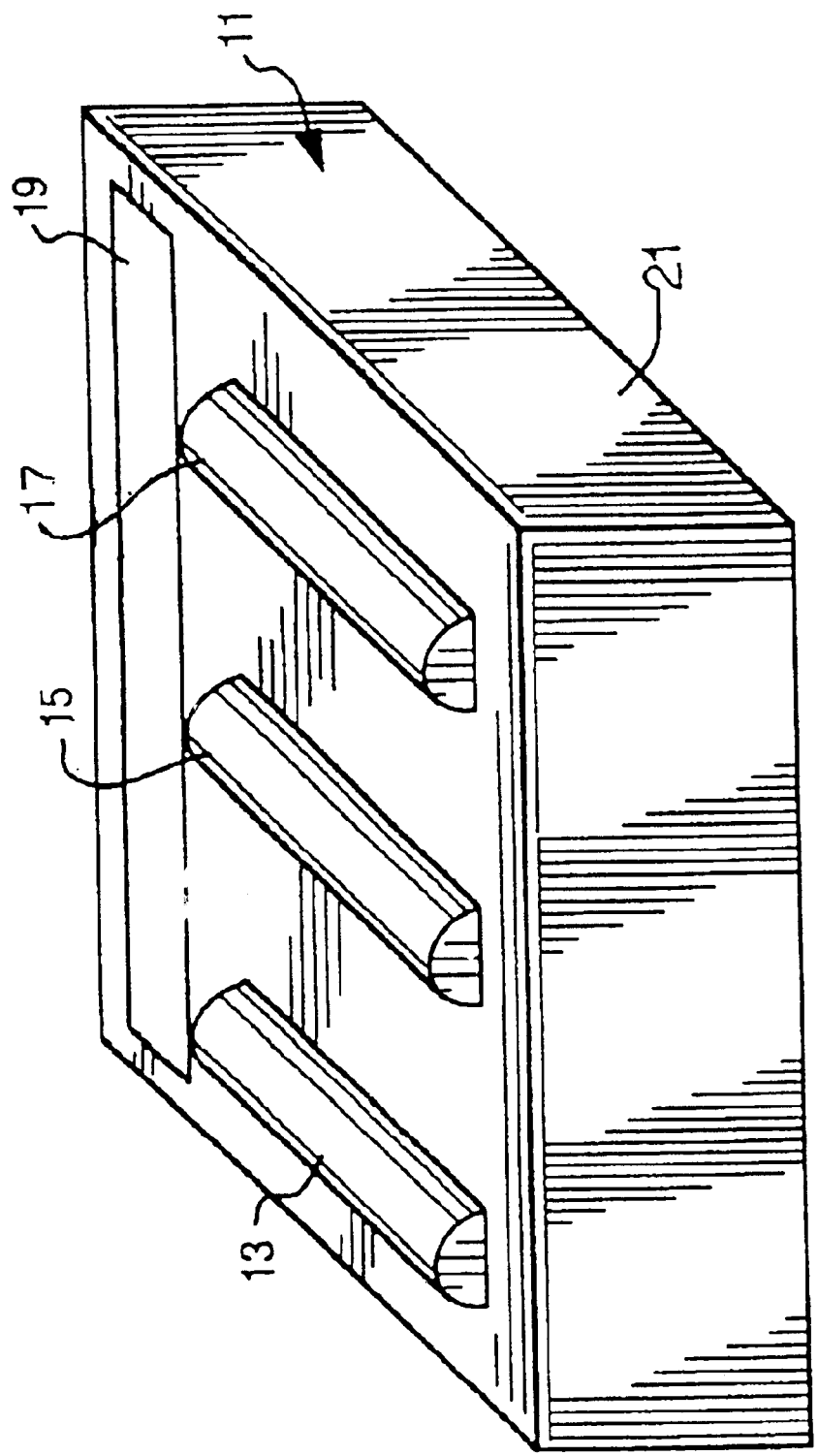
FIG. 1 depicts a kit having features of the present invention.

The present invention features methods, compositions, kits, and apparatus for determining the presence or absence of a target molecule. The target molecule may comprise any small or large organic molecules, peptides or proteins, the tertiary structure of nucleic acids or complex or simple carbohydrates the detection of which is desired.

This detailed description will begin with a close examination of one embodiment of the present invention. The composition comprises a first RNA molecule. The first RNA molecule binds a target molecule and has the following formula:

5'-A-B-C-D-E-3'.

As used above, A is a section of the RNA molecule having 10–100,000 nucleotides which section is, with another RNA sequence, E, replicated by an RNA replicase.

Preferably, the sequences represented by the letters "A" and "E" are selected from the group of sequences consisting of MDV-I RNA, Q-beta RNA microvariant RNA, nanovariant RNA, midivariant RNA, RQ-135 and modifications of such sequences which maintain the ability of the sequences to be replicated by Q-beta replicase. Preferably, the replicase is Q-beta replicase.

The sequence of MDV-I RNA has been widely reported. For convenience, it is presented below as Seq. ID No. 1.

Seq. ID No. 1

5' GGGGACCCCC CCGGAAGGGG GGGACGAGGU GCGGGCACCU

UGUACGGGAG UUCGACCGUG ACGCAUAGCA GGCCUCGAGA

UCUAGAGCAC GGGCUAGCGC UUUCGCGCUC UCCCAGGUGA

CGCCUCGUGA AGAGGCGCGA CCUCGUGCGU UUCGGCAACG

CACGAGAACC GCCACGCUGC UUCGCAGCGU GGCUCCUUCG

CGCAGCCCGC UGCGCGAGGU GACCCCCCGA AGGGGGGUUC

CCGGGAAUUC 3'.

A preferred sequence derived from MDV-I RNA for sequences represented by the letter A, is set forth below as Seq ID No. 2:

Seq. ID No. 2

5' GGGGACCCCC CCGGAAGGGG GGGACGAGGU GCGGGCACCU

UGUACGGGAG UUCGACCGUG ACGCAUAGCA GGAA UU 3'

A preferred sequence derived from MDV-I RNA for sequences represented by the letter E, is set forth below as Seq ID No. 3:

Seq. ID No. 3

5'-GGGGACCCCC CGGGCCUCGA GAUCUAGAGC ACGGGCUAGC

GCUUUCGCGC UCUCCCAGUG ACGCCUCGUG AAGAGGCGCG

ACCUUCGUGC GUUUCGGCAA CGCACGAGAA CCGCCACGCU

GCUUCGCAGC GUGGCUCCUU CGCGCAGCCC GCUGCGCGAG

GUGACCCCCC GAAGGGGGGU UCCC-3'

A preferred sequence derived from RQ-135 for sequences represented by the letter A, is set forth below as Seq ID No. 4:

Seq. ID No. 4

5'-GGGGUUUCCA ACCGGAAUUU GAGGGAUGCC UAGGCAUCCC

CCGUGCGUCC CUUUACGAGG GAUUGUCGAC UCUAGUCGAC-3'

A preferred sequence derived from RQ-135 for sequences represented by the letter E, is set forth below as Seq ID No. 5:

Seq. ID No. 5

5'-GGUACCUGAG GGAUGCCUAG GCAUCCCCGC GCGCCGGUUU

CGGACCUCCA GUGCGUGUUA CCGCACUGUC GACCC-3'

The letter "B" denotes a section of the RNA molecule having approximately 1 to 50000 nucleotides which section, with another sequence D, binds the target molecule under binding conditions. The letter "D" denotes a section of the RNA molecule having approximately 1 to 50000 nucleotides which section, with another sequence B, binds the target molecule under binding conditions. The sections B and D, in combination, comprise in total at least 10 nucleotides.

Preferably, the sections B and D have a combined total of 20–5,000 nucleotides and, even more preferred, 20–50 nucleotides. Preferably, the sections B and D bind to target through non-nucleic acid base pairing interactions. Sections B and D bind to the target in the manner of naturally occurring nucleic acid which form RNA-protein complexes. Or, the B and D sections are non-naturally occurring sequences which are selected to bind the target. These non-naturally occurring sequences are selected by computer modeling, or aptamers or partial aptamers, and other nucleic acids exhibiting affinity to the target.

The term "aptamer" is used in the manner of Klug, S. J. and Famulok, M. "All you wanted to know about SELEX", Molecular Biology Reports, 20:97–107 (1994) and other nucleic acids which are selected for affinity to a selected target. Aptamers are selected for a particular functionality, such as binding to small or large organic molecules, peptides or proteins, the tertiary structure of nucleic acids or complex or simple carbohydrates. The sequences for nucleic acids that bind to a polymerase, bacteriophage coat protein, serine protease, mammalian receptor, mammalian hormone, mammalian growth factor, ribosomal protein, and viral rev protein are disclosed in U.S. Pat. No. 5,475,096. The method presented in such patent may also be used to identify other aptamer sequences.

In addition, nucleic acids which bind to a target may also be identified by in vitro selection. After such nucleic acid has been selected and identified, such nucleic acid is sequence in a manner known in the art.

Preferably, the section B has a hybridization sequence of 1–100, and more preferred, 1–50, and most preferred, 1–5 nucleotides adjacent to the section A which form a hybridization product with a complementary hybridization sequence of section D. The nucleotides of the hybridization sequence of section D are adjacent section E. The hybridization sequences of sections B and D preferably define a loop or hairpin at such times that section B and D are bound to target. In the absence of target, the hybridization sequences do not form a stable hybridization product. In the presence of the target, and the formation of a complex between sections B and D with the target, a hybridization product is formed that allows the RNA replicase to skip sections B, C and D and replicate sections A and E.

The Example of this application uses nucleic acid which binds adenosine triphosphate (ATP). A preferred sequence for section B is set forth below as Seq. ID No. 6:

5'-AGUUGGGA AGAAACUGUG GGACUUCG-3' Seq ID No. 6

A preferred sequence for section D is set forth below as Seq. ID No. 7:

5'-GUCCCA GCAACU-3' Seq ID No. 7

The letter "C" denotes a section of the RNA molecule having approximately 1 to 10000 nucleotides which section is capable preventing the replication of the first molecule by the RNA replicase. Preferably, the section C has 1–10,000 nucleotides, and more preferred, 1–1000 nucleotides, and most preferred, 1–100 nucleotides which sequences define a stop sequence for the RNA replicase. Stop sequences or signals comprise one or more sequences which the RNA replicase can not read through to effect replication of the sequence. These sequences include, by way of example, without limitation, a sequence of poly A, poly C, poly G, multiple initiation sites, modified nucleotides which do not allow the RNA replicase to act on the sequence, sugar linkages without nucleotides and altered phosphate or sugar linkages.

A preferred stop sequence is such sequence recognized by the enzyme ricin and or sarcin. Ricin acts on such sequence to effect a modification of the nucleic acid, the removal of the base. Such a preferred sequence for the section C is set forth below as Seq ID No 8:

5'-AUGUACG AGAGGACC-3' Seq ID No. 8

The first RNA molecule, with sections B and D bound to target, is acted upon by the RNA replicase to form a second RNA molecule. The second RNA molecule has the following formula:

5'-E'-X-A'-3'.

As used above, E' is the complement to E, and A' is the complement to A. The letter "X" denotes the complement of parts of the sections B, C and D which may be replicated, or the letter denotes the direct bond between sections E' and A'.

The second RNA molecule is replicated by the RNA replicase under replicating conditions.

Preferably, the sections A and E comprise at least one sequence that hybridizes to a third nucleic acid. Such third nucleic acid forms a hybridization product which hybridization product can be detected by known means.

A second embodiment of the present invention features paired RNA molecules comprising a first RNA molecule. The first RNA molecule binds a target molecule and has the following formula:

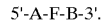
5'-A-F-B-3'.

And, the second RNA binds the target and has the following formula:

5'-D-H-E-3'

As used above, A is a section of the RNA molecule having 10–100,000 nucleotides which section is, with another RNA sequence, E, replicated by an RNA replicase. The letter "B" denotes a section of the RNA molecule having approximately 1 to 50000 nucleotides which section, with another sequence D, binds the target molecule under binding conditions. The letter "D" denotes a section of the RNA molecule having approximately 1 to 50000 nucleotides which section, with another sequence B, binds the target molecule under binding conditions. The sections B and D, in combination, comprise in total at least 10 nucleotides. The first RNA molecule, with sections B and D bound to target, is acted upon by the RNA replicase to form a third RNA molecule. The letter "F" denotes a section of the RNA molecule having has a hybridization sequence of 1–100, and more preferred, 1–50, and most preferred, 1–5 nucleotides which form a hybridization product with a complementary hybridization sequence of section H. The hybridization sequences of sections F and H preferably define a loop or hairpin at such times that section B and D are bound to target. In the absence of target, the hybridization sequences do not form a stable hybridization product. In the presence of the target, and the formation of a complex between sections B and D with the target, a hybridization product is formed that allows the RNA replicase to skip sections B and D and replicate sections A and E to form a third RNA molecule. The third RNA molecule has the following formula:

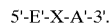
5'-E'-X-A'-3'.

As used above, E' is the complement to E, and A' is the complement to A. The letter "X" denotes the complement of parts of the sections B, F, H and D which may be replicated, or the letter denotes the direct bond between sections E' and A'. The third RNA molecule is replicated by the RNA replicase under replicating conditions.

Preferably, the sections F and/or H have 1–10,000 nucleotides, and more preferred, 1–1000 nucleotides, and most preferred, 1–100 nucleotides which sequences define a stop sequence for the RNA replicase.

A further embodiment of the present invention features a method of determining the presence or absence of a target molecule. The method comprises the steps of providing a first RNA molecule. The first RNA molecule is capable of binding to a target molecule and has the formula

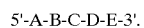
5'-A-B-C-D-E-3'.

The sections A, B, C, D and E are as previously described. The method further comprises the step of imposing binding conditions on a sample potentially containing target molecules in the presence of the first RNA molecule. In the presence of the target molecule, the first RNA molecule forms a target-first RNA molecule complex.

The second RNA molecule has the formula:

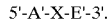
5'-A'-X-E'-3'.

The sections A', X and E' are as previously defined. It is believed that the RNA replicase skips sections B, C, and D as such sections are held, sterically hindered, by the target molecule.

Further binding between sections B and D by short sequences adjacent sections A and E facilitate skipping by bringing the template sections in close proximity to each other.

A second method comprises the steps of providing paired RNA molecules comprising a first RNA molecule and a second RNA molecule. The first RNA molecule is capable of binding to a target molecule and has the formula:

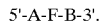
5'-A-F-B-3'.

The second RNA molecule has the formula:

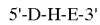
5'-D-H-E-3'

The sections A, B, D, E, F and H are as previously described. The method further comprises the step of imposing binding conditions on a sample potentially containing target molecules in the presence of the first RNA molecule and second RNA molecule. In the presence of the target molecule, the first RNA molecule and the second RNA molecule forms a target-first second RNA molecule complex. The method further comprises the step of imposing RNA replicase reaction conditions on the sample, in the presence of an RNA replicase, to form a third RNA molecule in the presence of target. The third RNA molecule has the formula:

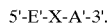
5'-E'-X-A'-3'.

As used above, E' is the complement to E, and A' is the complement to A. The letter "X" denotes the complement of parts of the sections B, F, H and D which may be replicated, or the letter denotes the direct bond between sections E' and A'.

Binding conditions are described by Gold L., Polisky B., Ulhlenbeck O, and Yarus M., (1995). In brief, binding conditions comprise room temperatures and 50 mM potassium acetate plus 50 mM Tris acetate, pH 7.5, 1 mM dithiothreitol The method further comprises the step of imposing RNA replicase reaction conditions on the sample, in the presence of an RNA replicase, to form a further RNA molecule in the presence of target. Reaction conditions for RNA replicases are known in the art. Q-beta replicase reactions are performed at 37° C. during 25–30 minutes in 50-ul reactions containing 88 mM Tris-HCL (pH 7.5), 12 mM MgCl$_2$, 0.2 mM of each ribonucleoside triphosphate, 25 uCi of [alpha-$^{32}$P]GTP, 90 pm/ml of Q-beta replicase, and 11.2 pm/ml of template RNA.

The sample is monitored for the presence of the third RNA molecule or its complement, which presence or absence is indicative of the presence or absence of the target molecule. The detection of RNA replicase templates is well known. Propidium iodine is commonly used as an intercalating agent to create a color change.

A further embodiment of the present invention comprises a kit for determining the presence or absence of a target molecule. The kit comprises a one or more reagents comprising a first RNA molecule for use with an RNA replicase. The first RNA molecule has the formula:

5'-A-B-C-D-E-3'.

In the presence of target, the first and the second RNA molecules are capable of forming a target-first-RNA complex and in the presence of an RNA replicase, forming a second RNA molecule having the formula:

5'-A'-X-E'-3'.

The letters A, B, C, D, E, A' E' and X are as previously described. The second RNA molecule is preferably capable of being replicated by Q-beta replicase.

A second embodiment of the kit for determining the presence or absence of a target molecule features paired RNA molecules. The kit comprises a one or more reagents comprising a first RNA molecule and a second RNA molecule. The first RNA molecule has the formula:

5'-A-F-B-3'.

The second RNA molecule has the formula:

5'-D-H-E-3'

In the presence of target, the first RNA molecule and the second RNA molecule are form a target-first-second RNA complex and in the presence of an RNA replicase, forming a third RNA molecule having the formula:

5'-A'-X-E'-3'.

The letters A, B, C. D, E, ,F, H, A' E' and X are as previously described. The third RNA molecule is preferably capable of being replicated by Q-beta replicase.

Turning now to FIG. 1, a kit, generally designated by the numeral 11, is depicted. The kit 11 comprises the first RNA molecule or paired RNA molecules contained in one or more vials 13, of which only one is shown, or means for making a first RNA molecule or paired RNA molecules. Preferably, the kit 11 has an RNA replicase illustrated as being contained in a second vial 15, suitable buffers and reagents illustrated as being contained in a third vial 17 and instructions 19. It is customary to package the elements of the kit 11 in suitable packaging such as box 21.

An embodiment of the present invention further comprises a method of making a first RNA molecule, wherein the first RNA molecule has the formula:

5'-A-B-C-D-E-3'.

As used above, the letters A, B, C, D, and E are as previously described. The method comprises the step of combining a sample containing the target molecule with a library of RNA molecules having the formula:

5'-A-B'-C-D'-E-3'.

to form a mixture of one or more target bound RNA molecules and one or more unbound RNA molecules. The letters B' and D' represent potential sections B and D. Next, primer nucleic acid corresponding to at least one section is added to the mixture with an enzyme capable of degrading the unbound RNA molecules. Next, bound RNA molecules are released from target and amplified to form an amplification product. Next, the RNA molecules comprising the amplification product having the formula:

5'-A-B'-C-D'-E-3' are sequenced. Or, a cDNA formed and such cDNA cloned into suitable vectors.

Preferably, the steps of forming a mixture, degrading unbound RNA molecules and amplifying the bound RNA molecules are repeated.

Preferably, the sections B' and D' are randomized nucleotides. Or, in the alternative, are generated through in vitro selection.

Preferably the step of degrading the unbound RNA molecules is performed in the presence of the enzyme reverse transcriptase. Methods and procedures for performing reverse transcriptase reactions are well known.

An embodiment of the present invention further comprises a kit for performing performing the above method of identifying first and second RNA molecules. The kit 11 has been described with respect to FIG. 1. The kit 11 comprises one or more nucleic acid molecules having sections corresponding to the sections A, B', C, D', and E. Preferably, the kit comprises sections B' and E' as randomized nucleotide sequences.

EXAMPLE 1

General Methods of Making Paired RNA Molecules

To construct the paired RNA molecules for the target analyte with a known ligand, two sets of the complementary oligonucleotide are designed and synthesized on a DNA synthesizer. One set of oligonucleotides is dsDNA representing the 5' part of the whole ligand. The other set of oligonucleotides is dsDNA representing the 3' part of the same ligand. Both dsDNAs are designed with terminal restriction enzyme sites for cloning in the vector, and with additional nucleotides with lengths from one to ten nucleotides. These additional sequences are selected to define stop sequences and sections F and H of such paired RNA molecules. The first dsDNA has the following formula: 5'-M--N--O--P-3'. The second dsDNA has the following formula: 5'-P--R--S--T-3', where M, P and T are restriction site linkers, O is sequences representing the 5' segment of the ligand, R is sequences representing the 3' segment of the ligand, and N and S are stop sequences.

Figure 2:
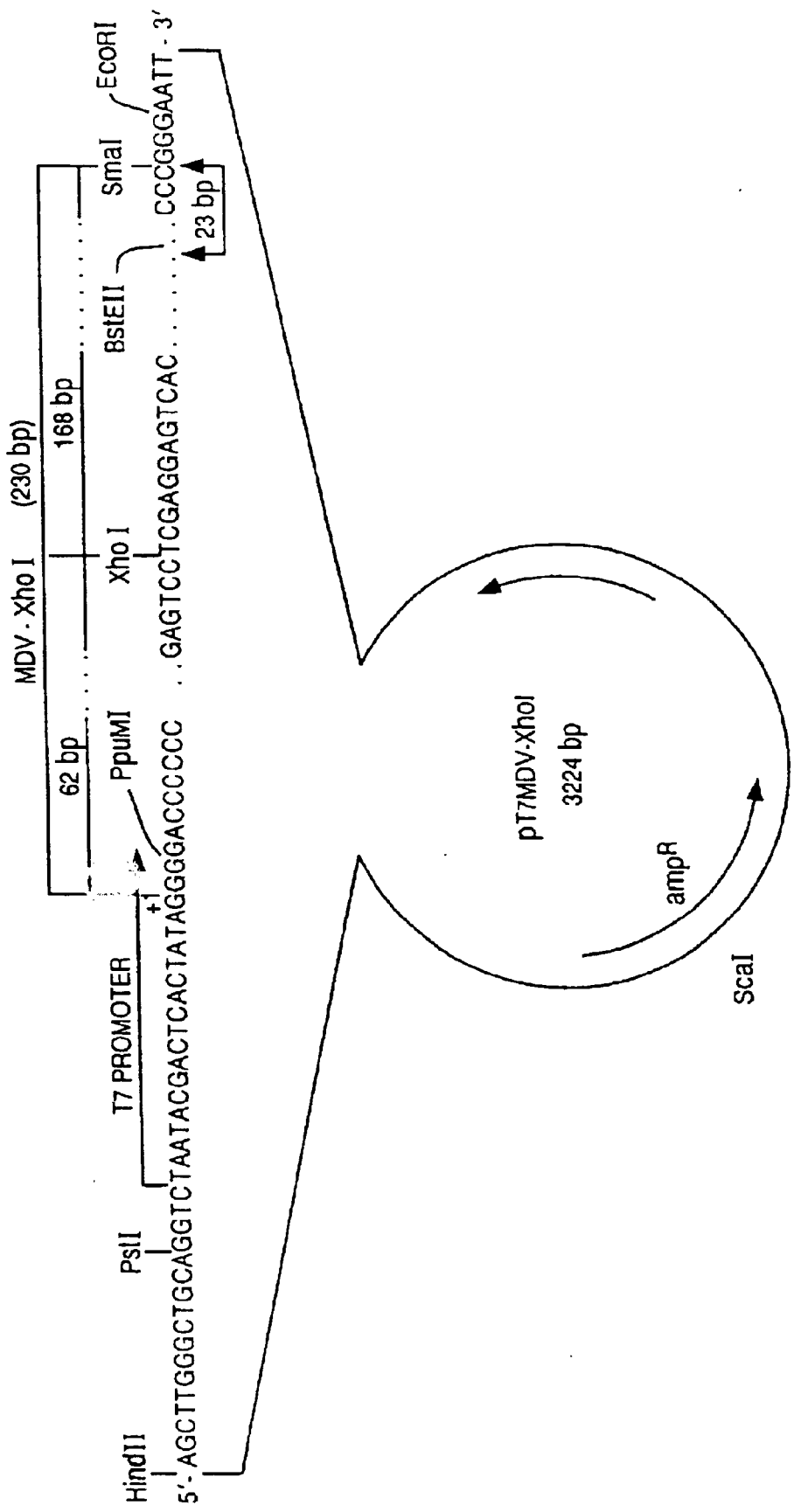
FIG. 2 depicts plasmid pT7 MDV-XhoI.
Figure 3:
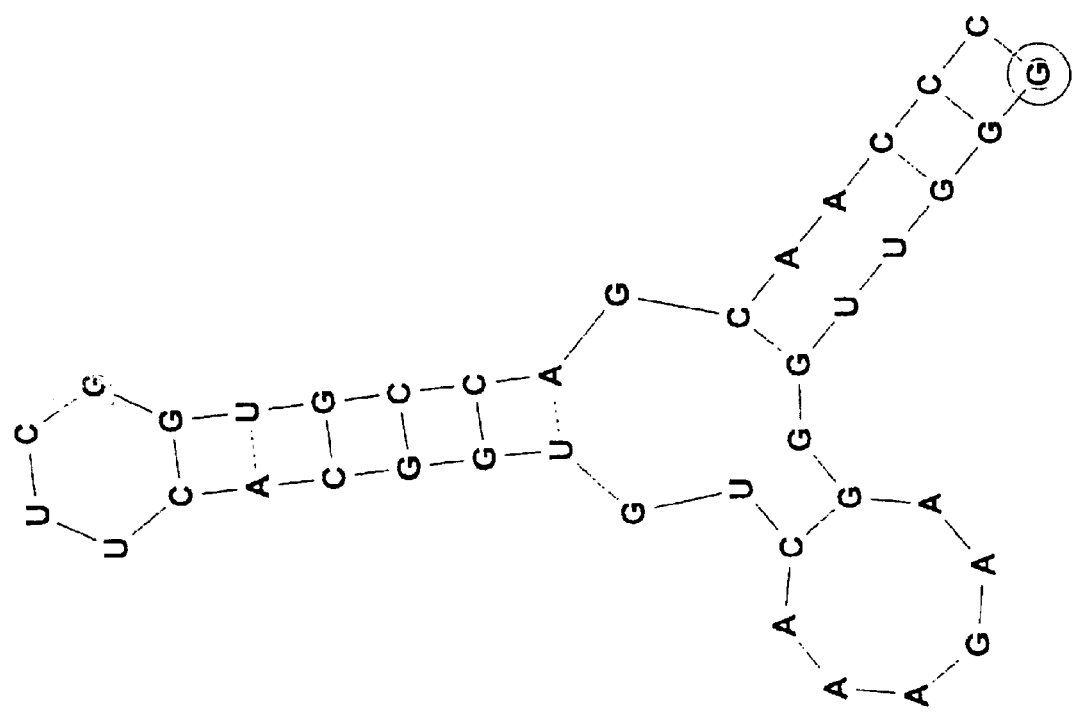
FIG. 3 depicts the binding element of an aptamer for ATP.
Figure 4:
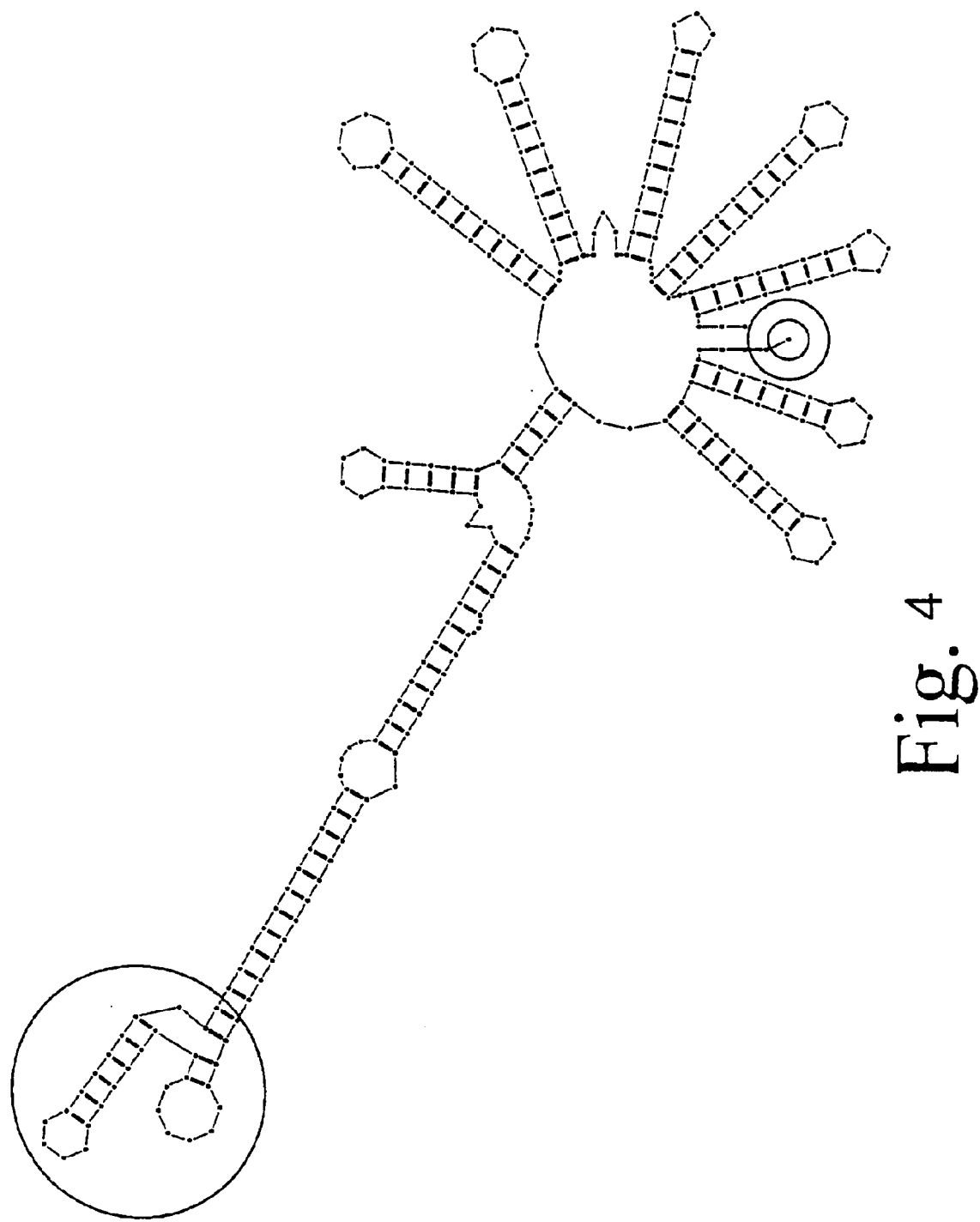
FIG. 4 depicts a modified MDV-1 template.

These two dsDNAs are cloned in a recombinant plasmid containing the T7 RNA promoter, followed immediately by inserting a Q-beta replicase template cDNA. A suitable cloning vector is disclosed in FIG. 2. Three unique restriction sites (M, P and T) for cloning dsDNA molecules are incorporated into the recombinant plasmid. One cloning site, M follows the T7RNA promoter immediately. The T cloning site is inserted into the end of the Q-beta replicase template, and the P site divides the template insert into two, 5' and 3', parts. Thus, the 5' part of the Q-beta replicase template is flanked by M and P restriction sites and 3' part of the template is flanked by P and T restriction sites.

The composition of the insert in such recombinant plasmid will be:

T7 promoter--M--Q-beta template--P--Q-beta template--T

A second recombinant plasmid is prepared by replacing the 5' part of the Q-beta replicase template cDNA situated between the M and P restriction sites with corresponding dsDNA representing the 5' segment of the ligand. The combined insert of the second recombinant plasmid has the following formula:

T7 promoter--M--N--P--Q-beta template--T.

A third recombinant plasmid is prepared by replacing the 3' part of the Q-beta replicase template cDNA situated between the P and T restriction sites with corresponding dsDNA representing the 3' segment of the ligand. The combined insert of the third recombinant plasmid has the formula:

T7 promoter--M--Q-beta template--P--S--T.

The second and third recombinant plasmids will be linearized by cleavage in the T restriction site, and the recombinant RNAs will be transcribed from each plasmid using the T7 RNA promoter.

Two recombinant RNA transcripts are formed.
The structure of the first detector-molecule is:

5'-A-F-B-3'.

And the structure of the second detector-molecule is:

5'-D-H-E-3'.

To form the single probe embodiment, essentially the same process is used, however, only one recombinant plasmid is formed encoding the entire first RNA molecule.

Recombinant plasmids containing the template sequences with the inserted sequences are used to transform competent bacterial cells, and the transformed cells are grown in a culture. The cultured cells are harvested and lysed. The DNA plasmids are purified. The recombinant plasmids are cleaved with an appropriate restriction enzyme and the recombinant Q-beta replicase templates containing the inserts of the original DNA are transcribed into the RNA using T7 RNA promoter. All procedures are performed according to the standard protocols of J Sambrook, E F Fritsch and T Maniatis (1989) known to someone skilled in the field of molecular biology.

EXAMPLE 2

Construction of RNA Molecules with MDV-1 Sequences and ATP Binding Sequences

This example describes the construction of RNA molecules with MDV-1 sequences and ATP binding sequences. An oligoribonucleotide, aptamer ATP-40-1, with a high-affinity to ATP molecules was identified (Sassanfar and Szostak, 1993). The sequence encoding ATP-40-1 aptamer, with an XhoI cloning site incorporated at the termini, is set forth in Seq ID No 9 below:

```
                                          Seq ID No 9
5'-TCGAGGGTTGGGAAGAAACTGTGGCACTTCGGTGCCAGCAACCC-3'

3'-CCCAACCCTTCTTTGACACCGTGAAGCCACGGTCGTTGGGAGCT-5'
```

Turning now to FIG. 3, the binding element of the original aptamer is composed of the 11-base consensus sequence and an unpaired G which is flanked by two base-paired stems. This aptamer is incorporated into plus-strand of the MDV-I RNA template using pT7MDV-1 recombinant plasmid with T7 RNA transcription promoter and standard molecular cloning procedures as depicted in FIG. 2 (Sambrook et al., 1989).

A computer analysis, with the program RNADRAW, suggested that the structural organization of the binding element of the original secondary structure of the ATP-40-1 aptamer remains intact when this aptamer fuses with plus-strand of Q-beta RNA templates. The secondary structures for ATP aptamer and for ATP-401/MDV-1 recombinant RNA as well as secondary structures of all further discussed RNA molecules were predicted by folding algorithms which showed only one of usually several alternative structures and RNA molecules of the same species with other structures might be present in a population.

The ATP aptamer sequences do not affect MDV-I RNA's ability to be amplified by Q-beta replicase, and the ATP aptamer-insert propagated in the recombinant RNA continues to demonstrate a high level of affinity to the original ligand, ATP. A 'short' wild-type amplification product was generated by Q-beta replicase together with a 'full length' amplification product when a recombinant RNA was used as a template. Apparently, Q-beta replicase does not always faithfully amplify the whole recombinant template with the ATP aptamer insert, but occasionally, with a frequency between 20% and 50%, skipped an insert and generate a wild type template.

Affinity of the synthesized recombinant template containing ATP specific RNA sequences to ATP was measured using the method for isocratic elution of labeled RNA from an ATP-agarose column (Sassanfar and Szostak, 1993). Nearly 100% of the recombinant RNA was collected from the 6B Sepharose column in the first two fractions. The same RNA, on the other hand, showed high affinity to the ATP-agarose. The elution rate slowed significantly after collecting the first four fractions. Addition of 4 mM ATP to the elution buffer increased the elution rate fourfold. This change in the elution rate could be explained by the competition between free ATP in the elution buffer and agarose-bound ATP for the ATP-binding insert in the recombinant RNA. Practically all of the labeled recombinant RNA used in this experiment was eluted with 3.5 ml of an elution buffer containing ATP. Completion of the elution was confirmed by treating the column with 10 mM EDTA. The lack of affinity of this recombinant MDV RNA to 6B Sepharose suggests that the affinity of this RNA to ATP-agarose is determined by the aptamer-insert, rather than by the flanking insert sequences of MDV RNA itself. Thus, two direct conclusions follow from these experiments. First, the ATP aptamer sequences do not affect MDV-I RNA's ability to be a template for Q-beta replicase. Secondly, the ATP aptamer-insert propagated in the recombinant RNA continues to demonstrate a high level of affinity to the original ligand, ATP.

EXAMPLE 3

This example describes the design and a construction of paired RNA molecules that will be used for ATP. Such paired RNA molecules will not generate an amplification product separately or when they will be used together in the presence of Q-beta replicase, ribo-nucleotide mix and an appropriate buffer since neither of the recombinant RNA molecules, nor two of them together, have a full and an intact complement of the replicatable, plus-strand, MDV-1 template.

The stability of such ternary complex formed in the presence of ATP is reinforced by a large number of paired nucleotides in RNA molecules. These regions of pairing will keep in close proximity two unbound terminal assembles of the paired RNA molecules as best seen in FIG. 4.

Furthermore, one region of RNA/ATP ternary complex will be protected from to be 'unzipped' by Q-beta replicase during template's amplification and Q-beta replicase will be able to use Region 1 as a 'bridge' and to skip the whole insert with a rate of 20–50%. Therefore, Q-beta replicase will be able to produce a functional minus-strand wild type MDV-1 template. This minus-strand will then serve as a template for wild type plus-strand in further replication. The presence of two wild type, plus and minus-templates assure an exponential amplification of RNA.

The sequence for the full length of the MDV-1 RNA is presented as Seq ID No 1. The coding DNA for this template was incorporated into the T7 MDV-1 plasmid depicted in FIG. 2. The bold letters in the MDV-1 RNA depict the cloning sites. MDV-1 RNA has the following cloning sites: PpuMI site (GGGACCC) at the 5' end of the template followed the T7 RNA transcription promoter, Eco1471 (AGGCCU), Xho I (CUCGAG), Bgl II (AGAUCU) and Xba I (UCUAGA) represented a multicloning site in the middle of the molecule. Two cloning sites, Sma I (CCCGGG) and Eco RI (GAAUUC) are in the 3' end of the molecule.

Each recombinant RNA molecule will consist of two parts, sequences of ATP aptamer and of MDV-1 template. The nucleotide sequences for an original ATP-40-1 aptamer is set forth in Seq ID No. 9 (Sassanfar and Szostak, 1993). This sequence was modified in the following manner. An A-U pair was introduced into one double-stranded region and one of the G-C pair was substituted for a pair C-G in the same position. The terminal loop, which in an original aptamer was represented by four nucleotide, UUCG, were changed to ten nucleotides, AAAGAAUUGG. The first RNA molecule of the paired RNA molecules will have nucleotide sequence set forth in Seq ID No 10:

```
                                           Seq ID No. 10
5' GGGGACCCCC CCGGAAGGGG GGGACGAGGU GCGGGCACCU

UGUACGGGAG UUCGACCGUG ACGCAUAGCA GGaguuggga agaaacugug ggacuucgAA UU 3'
```

The capital letters depict the 5' segment of MDV-1 template; the small bold letters depict the sequences of the ATP that will substitute a 3' segment of the MDV-1 template and to be cloned between Eco 1471 and Eco RI cloning sites of the plasmid.

The second recombinant RNA molecule will have nucleotide sequence set forth in Seq ID No. 11:

```
                                           Seq ID No. 11
5'-GGGGACCCCC CGGGguccca gcaacuCCUC GAGAUCUAGA

GCACGGGCUA GCGCUUUCGC GCUCUCCCAG UGACGCCUCG

UGAAGAGGCG CGACCUUCGU GCGUUUCGGC AACGCACGAG

AACCGCCACG CUGCUUCGCA GCGUGGCUCC UUCGCGCAGC

CCGCUGCGCG AGGUGACCCC CCGAAGGGGG GUUCCC-3'.
```

The capital letters depict the 3' segment of MDV-1 template; the small bold letters depict the sequences of the ATP that will substitute a 5' segment of the MDV-1 template and to be cloned between Eco 1471 and PpuMI cloning sites of the plasmid.

Figure 5A:
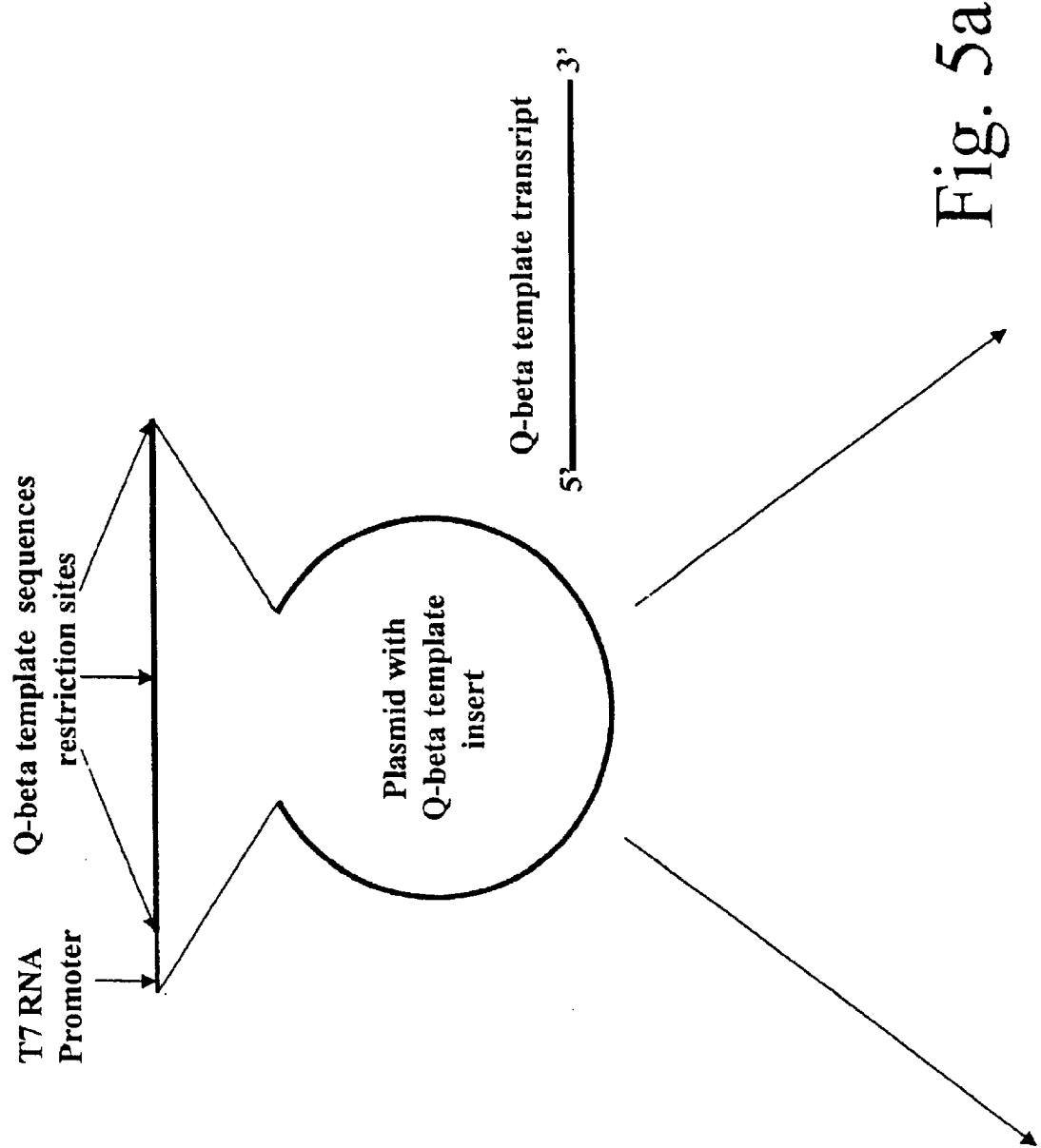
FIGS. 5a, 5b, and 5c depict plasmid construction.
Figure 5B:
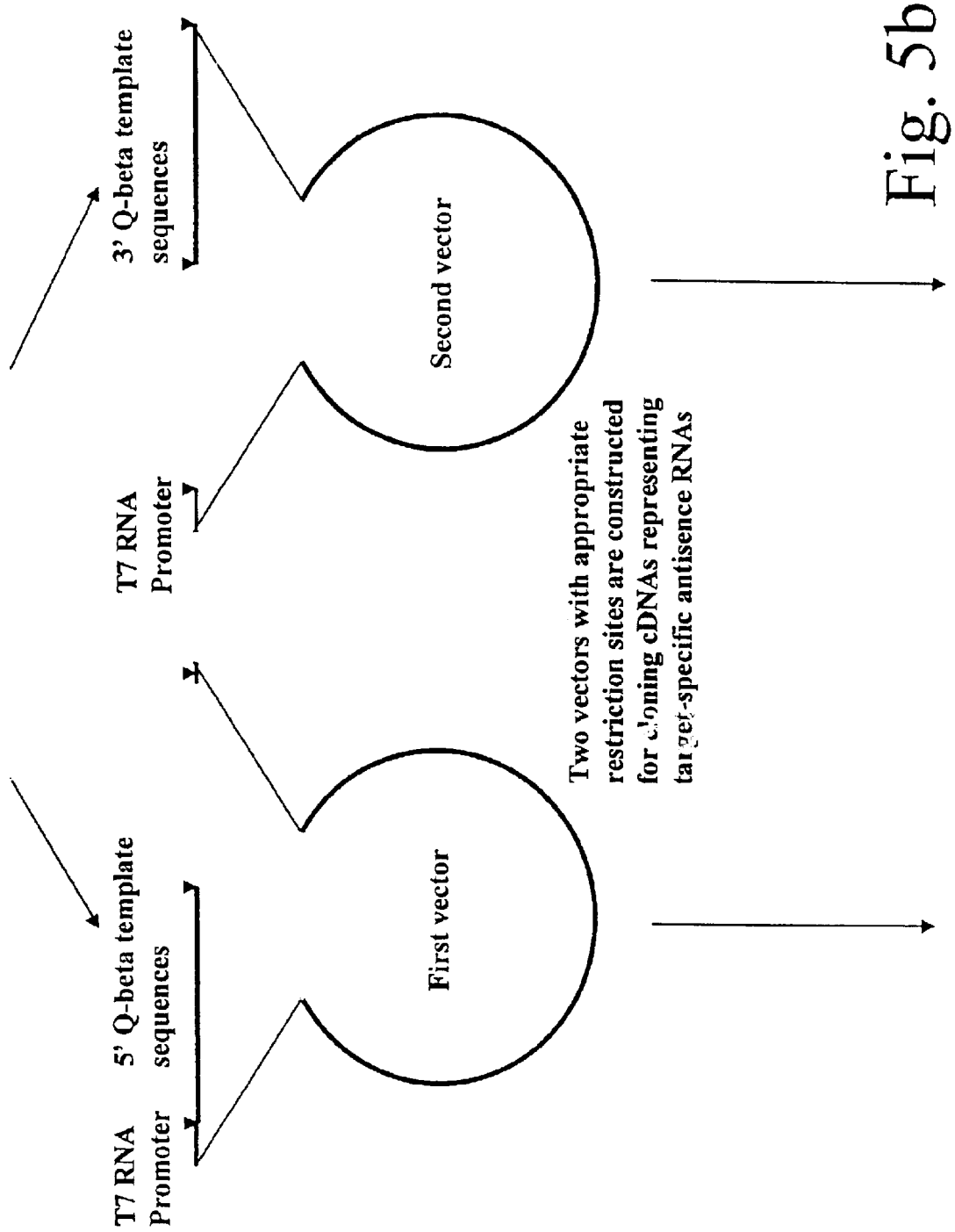
Figure 5C:
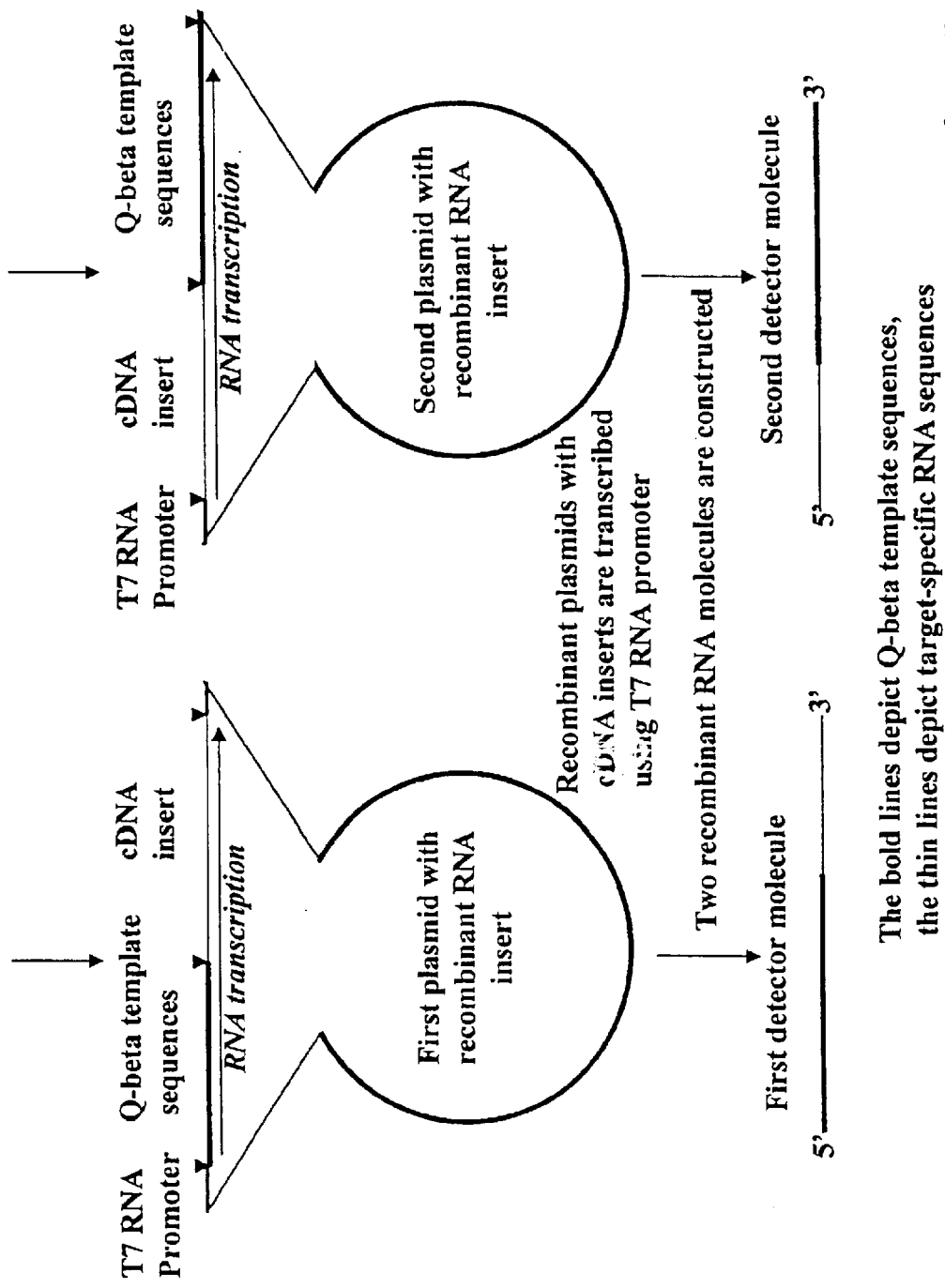

The construction of the recombinant RNA molecules is performed following standard cloning procedures. The synthesis of the designed recombinant RNAs is outlined in FIG. 5. The construction of the recombinant RNAs will start with the pT7 MDV-1 recombinant plasmid containing T7 RNA polymerase promoter, and DNA inserts representing MDV-1 template and restriction sites, described above. The plasmid DNA will be double-digested either with PpuMI and Eco 1471 or with Eco 1471 and Eco RI restriction enzymes and purified from the excised fragments. The linearized cloning vectors will be annealed with synthetic cDNAs representing ATP-specific RNA sequences with appropriate cohesive ends and ligated with T4DNA ligase. Recombinant plasmids with desired cDNA inserts will be amplified and then transcribed using T7RNA polymerase promoter following the standard procedures (Sambrook et al., 1989). The RNA transcripts will be purified either by polyacrylamide gel (PAGE) or commercially available RNA purification kits.

We anticipate that paired RNA molecules together with ATP will form a ternary structure, where the two RNA molecules will acquire a conformation similar to the native ATP aptamer, i.e. an asymmetrical bulge flanked by two double-stranded segments. The hybridized recombinant RNAs will have a terminal gap between them that will prevent replication. However, the interaction of an ATP molecule with two recombinant RNA molecules will be strong enough to secure the stability of the double-stranded regions and to promote synthesis of a functional wild type MDV-1 template under Q-beta replicase reaction conditions. The wild-type MDV-1 template is the amplification product of interest.

The reaction is performed at 37° C. in solutions containing Tris-HCl (pH 7.5), a mixture of ribonucleoside triphosphate, appropriate Mg- and Na-salts, and Q-beta replicase enzyme. The concentrations of reaction mix components, such as triphosphates, $MgCl_2$ and NaCl, template/Q-beta replicase molar ratios are varied to achieve optimal conditions under which the maximal yield of the minus-strand templates and amplified product will be reached. The actual number of templates in the reaction can be estimated by adding the sample to a standardized reaction mixture and measuring the time required to produce a signal with an intercalating fluorescent dye. The response time is universally proportional to the log of the number of template molecules present in the sample (Lomeli et al., 1989).

There are several nucleotide modifications for fluorimetric assays that can be easily used by Q-beta replicase enzyme for RNA amplifications. One such compound is 8-azidoadenosine 5'-triphosphate (8-azido ATP), which could be incorporated into the replicated RNA and is useful in reactions with different fluorochromes (Czarnecki et al., 1979). Another modified nucleotide is 4-thiouridine 5'-diphosphate (4-thio UTP) which also could be incorporated into replicated RNA by Q-beta replicase. Consequently, 7-fluoro-2,1,3-benz-oxadiazole-4-sulfonamide might be used as a reagent for fluorometric identification of the thiol group in the incorporated thionucleotides (Toyooka and Imai, 1984). The amplified recombinant RNA templates can be also identified and quantified by various easily available fluorescent dyes, such as ethidium bromide or RiboGreen (Molecular Probes Inc.), which produce a fluorescent signal upon intercalation into base-paired double stranded regions of the amplified RNA.

For quantification of the template in the reaction mix, 5-ul aliquots are removed at 5 min intervals and mixed with ice-cold 90% formamide containing 50 mM Tris-borate (pH 8.2), 2 mM EDTA, 1 ug/ml carrier tRNA. From this mixture, from seven to 15 ul are applied directly onto magnesium-containing PAGE for visual analysis of the amplification product. For fluorescent analysis, the amplification reaction is filtered through DE81 (ion exchange) filters. The filters is washed two times with 5 ml buffer containing 50 mM Tris-HCl ph 7.5, 100 mM NaCl, 2 mM $MgCl_2$ and 1 mM EDTA. The bound material is eluted with 5 ml buffer containing 50 mM Tris-HCl ph 7.5, 500 mM NaCl, 2 mM MgCl$_2$ and 1 mM EDTA and collected. The filters, eluates and washing buffer are collected and fluorimetrically assayed. Aliquots of each amplification reaction are taken at 1 min intervals, and the RNA in each aliquot assessed using the fluorescence of the amplified detector molecules by photography over an ultraviolet light box, or measured in a fluorometer.

EXAMPLE 4

This example describes paired RNA molecules composed of Sarcin/Ricin and Rev protein specific sequences and RQT template sequences. The sequences specific for Sarcin and Ricin allow the formation of stop sequences and allow further stabilization of the tertiary complex. That is, the paired RNA molecule have two, tandemly-arranged RNA aptamer sequences. Each aptamer sequence has affinity to a different target, either Rev protien or Sarcin/Ricin. The paired RNA detector molecules with two recognition sites will bind with two targeted molecules and will form a quadruple complex of two RNAs and two targets. Such quadruple RNA/target complex will be more rigid structurally than a 'two RNAs/single target' ternary complex and, thus, will reinforce the stability of the double stranded regions. The double stranded regions and the stable ternary complex will facilitate the generation of a wild type minus-strand replicatable template.

The recombinant pT7 RQT plasmid with DNA encoding RQT RNA, depicted in FIG. 6, was constructed in our lab. The RNA sequence of RQT RNA is set forth in Seq ID No. 12 as follows:

Seq ID No. 12
5'-GGGGUUUCCA ACCGGAAUUU GAGGGAUGCC UAGGCAUCCC

CCGUGCGUCC CUUUACGAGG GAUUGUCGAC UCUAGAGGAU

CCGGUACCUG AGGGAUGCCU AGGCAUCCCC GCGCGCCGGU

UUCGGACCUC CAGUGCGUGU UACCGCACUG UCGACCC-3'.

The bold letters in the previous sequence depict three cloning sites XbaI, Bam HI and KpnI.

The Sarcin/Ricin (S/R) specific region of the above sequence includes a near universal sequence for all of 23S rRNA sequence. This region comprises 12 ribonucleotides with a define secondary structure that appeared as a single terminal loop (Munishkin and Wool, 1997. Treatment of this oligonucleotide with low concentrations of alpha-Sarcin or Restrictocin generated two fragments as a result of the cleavage of the oligonucleotide by this protein in a specific site between G and A nucleotides (Wool, 1997 and Related Work). The same domain of 28S rRNA is a target for another, more notorious, toxin--ricin. Ricin, however, inactivates ribosomes by depurination of the A residue, which is upstream and next to the alpha-Sarcin target site (Marchant and Hartley, 1995). Ribosomes are extremely sensitive to the toxins. The K$_d$s for the binding of the sarcin or ricin toxin to the S/R oligonucleotide are in the range of 10$^{-8}$ M (Wool, 1997).

Human Immunodeficiency Virus type-1 Rev protein binds with high affinity to a bulge structure located within the Rev-response element (RRE) RNA, Rev protein-specific ligand RBC5L. The smallest oligoribonucleotide able to bind Rev protein with 1-to-1 stoichiometry and with high affinity (K$_d$s of approximately 5 nM) carries the bulge and two sets of four flanking base pairs. The bulge structure contains a specific configuration of non-Watson-Crick G:G and G:A base pairs and demonstrates high affinity recognition of Rev protein by hydrogen bonding to the functional groups in the major groove of the Rev binding element. Introducing truncation and base pair modifications of the double stranded regions that flank the bulge did not affect the affinity or specificity of the original ligand, as long as the nucleotide sequence of the bulge itself was not changed.

A recombinant RQT template with two heterologous RNA inserts, Rev protein-specific RNA sequences and R/S rRNA domain, organized in a tandem fashion was made. Using the ability of alpha-Sarcin and Restrictocin to cleave the Sarcin domain RNA between G and A nucleotides we generated two RNA molecules. A first RNA molecule has nucleotide sequence set forth in Seq ID No. 13:

Seq ID No. 13
5'-GGGGUUUCCA ACCGGAAUUU GAGGGAUGCC UAGGCAUCCC

CCGUGCGUCC CUUUACGAGG GAUUGUCGAC UCUAGucgac gucugggcga aaaFake it out-3'

The 5' portion of the first RNA molecule corresponds to RQT template sequences set forth in Seq ID No. 4. The sequence gucugggcg corresponds to one half of the Rev-specific ligand. The sequence uaguacgag corresponds to a portion of the Sarcin specific RNA domain.

A second RNA molecule has a sequence set forth in Seq ID. No. 14:

5'-aggaccuuuu cgguacagac GGUACCUGAG GGAUGCCUAG
GCAUCCCCGC GCGCCGGUUU CGGACCUCCA GUGCGUGUUA
CCGCACUGUC GACCC-3'

The 3' portion of the second RNA molecule corresponds to RQT template sequences set forth in Seq ID No. 5. The sequence aggacc corresponds to a portion of the Sarcin-specific domain. The sequence cgguacagac corresponds to one half of the Rev-specific ligand. These two recombinant RNA molecules can be used as paired RNA molecules for the detection of one of the cytotoxins, such as Sarcin, Ricin or Restrictocin, in the presence of Rev protein, in a sample.

Treatment of the recombinant RQT template that incorporates Rev protein-specific RNA sequences and alpha-Sarcin domain synthetic nucleotides with different concentrations of Sarcin or Restrictocin showed that almost a perfect cleavage of the recombinant template with a production of two RNA fragments, with expected sizes of 99 nt and 103 nt. About 85% of the substrate was cleaved with a single cut of either enzyme at concentration of 25 ug/ml (14.7×10$^{-7}$M). Higher concentrations of Sarcin or Restrictocin led to non-specific cleavage of the recombinant RTQ template in numerous sites. Similar results were reported when a synthetic 35-mer oligoribonucleotide with nucleotide sequences and the secondary structure of the Sarcin domain was treated with Sarcin (Wool, 1997). The two recombinant RNAs generated as a result of the Sarcin or Restrictocin treatments are purified, either by polyacrylamide gel (PAGE) or commercially available RNA purification kits.

RNA duplex formed as a result of hybidization of the constructed two recombinant RNA molecules is structured in the whole length of the RQT sequences and unstructured in the binding with the Rev protein and Sarcin targets region. Hybridization of two RNA molecules is performed in a standard renaturation buffer containing 10 mM Tris-HCl, pH 7.6, 50 mM NaCl and 10 mM MgCl$_2$ with final concentration of RNA molecules in a range of 30 ng/ul. The solution with RNA molecules is boiled for 2 min and then chilled to room temperature. The optimal concentration of two RNA molecules and their molar ratios are determined empirically.

The RNA complex composed of two hybridized RNA molecules is with either Rev protein or Sarcin and placed under binding conditions. An annealing reaction of RTQ Rev/Sar RNA for Rev protein is performed in 10 mM Hepes/KOH buffer, pH 7.8, containing 100 mM KCl, 2 mM MgCl$_2$, 0.5 mM EDTA, 1 mM DTT and 10% Glycerol. An annealing reaction of RQT Rev/Sar RNA with Sarcin and Restrictocin is performed in reaction mix containing 10 mM Tris-HCl buffer, pH 7.6, 50 mM KCl and 4 mM EDTA. The binding complex of Rev protein and hybridized paired RNA molecules will be separated from the unbound molecules by filtration through nitrocellulose membrane filters (Tuerk and Gold, 1990).

The complex is then subjected to Q-beta replicase reaction conditions. The sample is monitored for the presence of wild type templates which are indicative that the enzyme has skipped the bound parts of the molecule.

EXAMPLE 5

This example features the construction of paired RNA molecules using Sarcin or Restrictocin as an agent that will cut a single recombinant RNA molecules into two parts. This method has the following major steps: (1) a cloning a single DNA into an available recombinant plasmid encoding Q-beta template sequences, (2) a transcription of the total length of the recombinant template RNA with the proper heterologous inserts, and (3) cleavage of the recombinant template into two parts using appropriate agent.

This simple protocol can be tailored to construct paired RNA molecules to identify any non-nucleic acid target that demonstrates affinity to the particular RNA sequence. Cleavage of a single RNA into first and second paired RNA molecule can be performed with some ribozymes or oligozymes.

Using standard cloning procedures, dsDNA represented Rev/Sarcin specific RNA sequences is cloned into pT7RQT plasmid using Kpn I/Xba I as a cloning sites. The new recombinant plasmid is linearized with Sma I restriction enzyme. Recombinant RNA that combined RQT, S/R and Rev protein specific RNA sequences, RQT Rev/Sar RNA, is transcribed using T7 RNA transcription promoter. The RNA sequences of the recombinant RQT RNA template with Rev-Sarcin specific insert are set forth in Seq ID No. 15:

```
                                 Seq ID No. 15
5'-GGGGUUUCCA ACCGGAAUUU GAGGGAUGCC UAGGCAUCCC
CCGUGCGUCC CUUUACGAGG GAUUGUCGAC UCUAGucgac
gucugggcga aaaauguacg agaggaccuu uucgguacag
acGGUACCUG AGGGAUGCCU AGGCAUCCCC GCGCGCCGGU
IJUCGGACCUC CAGUGCGUGU UACCGCACUG UCGACCC-3'.
```

The capital letters in the sequence above depict the nucleotides of the RQT templates, with the bold capital letters indicating the restriction sites. The small bold letters depict the Rev protein. The small, bold italic letters depict Sarcin specific RNA sequences. The Sarcin specific sequences are positioned within the sequences associated with Rev protein specific sequences. The combined Rev- and Sarcin-specific sequences is modified slightly from those reported earlier by eliminating some paired nucleotides and introducing a- and u-tetramers and UCGAC nucleotides to promote proper orientation as suggested by computer modeling. Both inserts are recognizable in the sense such molecules exhibit binding and/or are acted upon by the corresponding Rev protein, Sarcin or Restrictocin molecules.

Annealing of RTQ Rev/Sar with Rev protein is performed in 10 mM Hepes/KOH buffer, pH 7.8, containing 100 mM KCl, 2 mM MgCl$_2$, 0.5 mM EDTA, 1 mM DTT and 10% Glycerol. A gel mobilty shift assays suggests that RBC5L RNA (control aptamer) was found to form a stable ribonucleoprotein complex in an excess of the Rev protein. The Rev protein specific sequences incorporated into the RQT template continue to recognize the target Rev protein.

Treatment of RQT Rev/Sar RNA with Sarcin and Restrictocin was performed in a reaction mix containing 10 mM Tris-HCl buffer, pH 7.6, 50 mM KCl and 4 mM EDTA. The same amount of internally $^{32}$P-labeled RQT Rev/Sar RNA was treated with Sarcin or Restrictocin in concentrations of 2, 10 and 25 ug/ml. Products of the reaction were tested on 12% denatured PAGE with 7M Urea. The data suggest the amount of two RNA fragments of 95 and 102 nt is increased with the increase of the concentration of the either cytotoxin. The recombinant template is subjected to amplification by Q-beta replicase to produce a wild-type amplification product.

References Cited

U.S. Patent Documents

Cech T R., Murphy F L., Zaug A J., Grosshans C., 1992. RNA ribozyme restriction endonucleases and methods. U.S Pat. No. 5,116,742

Gold L. and C. Tuerk. 1995. Nucleic Acid Ligands. U.S. Pat. No. 5,475,096

Gold L. and S. Rinquist. 1996. Systematic Evolution of Ligands by Exponential Enrichment: Solution SELEX. U.S. Pat. No. 5,567,588.

Hazeloff J P., Gerlach W L., Jennings P A., Cameron F H. 1993. Ribozymes. U.S. Pat. No. 5,254,678.

Martinelli R A., Donahue J J. and Unger T. 1995. Amplification of Midivariant DNA Templates. U.S. Pat. No. 5,407,798

Roberson H D., and Goldberg A R., 1993. Ribozyme Composition and Methods for Use U.S. Pat. No. 5,225,337

Other Publications

Axelrod V A., Brown E., Priano C. and Mills D R. 1991. Virology, 184, 595–608

Bock et al., 1992, Bock L C., Griffin L C., Lathman J A., Vermaas E H. and Toole J J. 1992. Nature. 355, 564–566.

Dobkin C., Mills D R., Kramer F R. and Spiegelman S. 1979. Biochemistry, 18, 2038–2044.

Engler M J. and Richardson C C. 1982. The enzymes. Academic Press, Inc. vol XV. 3–29.

Fernandez A., 1991. Z. Naturforsch C. 46, 656–662.

Gold L., Polisky B., Uhlenbeck O, and Yarus M. 1995. Ann. Rev. Biochem. 64, 763–797.

Joyce, G F. 1989. Gene, 82, 83–87.

Kaufmann G., Klein T. and Littauer U Z. 1974. FEBS Lett. 46, 271–275.

Klug S J. and Famulok M. 1994. Mol. Biol. Rep., 20, 97–107

Kubik M F., Stephens A W., Schneider D., Marlar R A. and Tasset D. 1994. Nucleic Acid Res., 22, 2619–2626.

Leis J., Silber R., Malathi V G. and Hurwitz J. 1972. "Advances in the Biosciences" (G. Raspe, ed) Pergamon, New York. vol. VIII, 117

Lizardi P M., Guerra C E., Lomeli H., Tussie-Luna I. and Kramer F R. 1988. Biotechnology, 6, 1197–1202.

Meselson M. and Yuang R. 1968. Nature, 217, 1110–1114

Mullis K B, Faloona F, Schraft, Saiki R K, Horn G and Erlich H A. 1986. CSH Symp. Quant Biol., 51, 263–273

Munishkin A V., Voronin L A., Ugarov V I., Bondareva L A., Chetverina H V. and Chetverin A B. 1991. J. Mol. Biol. 221, 463–472.

Nakamura R M. 1993. College of American Pathologists Conference XXIV on Molecular Pathology: Introduction. Ach. Path. Lab. Med., 117, 445–492

Pieken W A., Olsen D B., Bensler F., Aurup H. and Eckstein F. 1991. Science. 253, 314–317.

Priano C., Kramer F R and Mills D R. 1987. Cold Spring Harbor Symp. Quant. Biol. 52, 321–330.

Pritchard C G. and Stefano J E. 1990 Ann. Biol. Clin. 48, 492–497.

Qi An, Buxton D, Hendricks A, Robinson L, Shah J, Ling Lu, Vera-Garcia V, King V and Olive M D. 1995. J. Clin. Microbiol., 33, 860–867

Saiki R K, Scharft S, Faloona F et al., 1985. Science., 230, 1350–1354.

Sambrook J., Fritsch E F and T. Maniatis. 1989. Molecular Cloning. Cold Spring Harbor Laboratory Press.

Schneider D J., Feigon J., Hostomsky Z. and Gold L. 1995. Biochemistry. 34, 9599–9610.

Silber R. Malathi V G. and Hurwitz J. 1972. Proc. Natl. Acad. Sci. USA 69, 3009–3013

Southern E, 1975. J. Mol. Biol., 98, 503–517.

Sugino A., Goodman H M., Heyneker H L., Shine J., Boyer H M. and Cozzarelli N R. 1977. J. Biol.Chem. 252, 3987–3987

Tuerk C. and Gold L. 1990. Science. 249.505–510.

Tyagi S., Landergen U., Tazi M., Lizardi P M. and Kramer F R. 1996. Proc. Natl. Acad. Sci. USA. 93, 5395–5400.

Rys P N and Persing D H. 1993. J Clin Microbiol., 31, 2356–2360.

Saiki R K. 1990. PCR Protocols: a Guide to Methods and Applications. M. A. Innis, D. H. Gelfand. J. J. Sninsky and T. J. White eds. (New York: Academic Press, Inc.), 13–20 Saiki R K, ScharftS, Faloona F et al., 1985. Science., 230, 1350–1354.

Sambrook J., Fritsch E F and T. Maniatis. 1989. Molecular Cloning. Cold Spring Harbor Laboratory Press.

Schneider D J., Feigon J., Hostomsky Z. and Gold L. 1995. Biochemistry. 34, 9599–9610.

Silber R. Malathi V G. and Hurwitz J. 1972. Proc. Natl. Acad. Sci. USA 69, 3009–3013

Southern E, 1975. J. Mol. Biol., 98, 503–517.

Sugino A., Goodman H M., Heyneker H L., Shine J., Boyer H M. and Cozzarelli N R. 1977. J. Biol.Chem. 252, 3987–3987

Tuerk C. and Gold L. 1990. Science. 249. 505–510.

Tyagi S., Landergen U., Tazi M., Lizardi P M. and Kramer F R. 1996. Proc. Natl. Acad. Sci. USA. 93, 5395–5400.

Uhlenbeck O C, and Gumport R D. 1982. The enzymes. Academic Press, Inc. vol XV. 31–58.

Uhlenbeck O C. 1983. TIBS. March, 94–96.

Verma I M. 1991. The Enzymes, The Academic Press, vol XIV, 87.

Weissmann C., Feix G. and Slor H. 1968. Cold Spring Harbor Symp. Quany. Biol. 33, 83–100.

Wu Y., Zhang D Y. and Kramer F R. 1992. Proc. Natl. Acad. Sci. USA. 89, 11769–11773.

Ziff E B. and Evans R M. 1978. Cell 15, 1463–1475.

What is claimed is:

1. A composition for determining the presence or absence of a target molecule comprising a first ribonucleic acid (RNA) molecule, said first RNA molecule binds a target molecule and has the following formula:

5'-A-B-C-D-E-3';

wherein A is a section of the RNA molecule having 10–100,000 nucleotides which section is, with another RNA sequence, E, replicated by an RNA replicase, the letter “B” denotes a section of the RNA molecule having approximately 1 to 50000 nucleotides which section, with another sequence D, binds the target molecule under binding conditions, wherein said target is a small or large organic molecule selected from the group consisting of a peptide, protein, and derivatives thereof, the letter “C” denotes a section of the RNA molecule having approximately 1 to 10000 nucleotides which section is capable preventing the replication of the first molecule by the RNA replicase, the letter “D” denotes a section of the RNA molecule having approximately 1 to 50000 nucleotides which section, with another sequence B, binds the target molecule under binding conditions, the sections B and D, in combination, comprise in total at least 10 nucleotides, the first RNA molecule, with sections B and D bound to target, is acted upon by the RNA replicase to form a second RNA molecule, said second RNA molecule has the following formula:

5'-E'-X-A'-3';

wherein, E' is the complement to E, and A' is the complement to A, and the letter “X” denotes the complement of parts of the sections B and D which may be replicated, or the letter denotes the direct bond between sections E' and A', and said second RNA molecule is replicated by the RNA replicase under replicating conditions.

2. The composition of claim 1 wherein the sections represented by the letters “A” and “E” are selected from the group of sequences consisting of MDV-I RNA, Q-beta RNA microvariant RNA, nanovariant RNA, midivariant RNA, RQ-135 and modifications of such sequences which maintain the ability of the sequences to be replicated by Q-beta replicase.

3. The composition of claim 1 wherein the RNA replicase is Q-beta replicase.

4. The composition of claim 1 wherein the sections B and D bind to target through non-nucleic acid base pairing interactions.

5. The composition of claim 1 wherein the sections B and D each have a hybridization sequence of 1–100 nucleotides, said hybridization sequence of section B is adjacent to the section A and forms a hybridization product with a said hybridization sequence of section D, and said hybridization sequence of section D is adjacent section E.

6. The composition of claim 1 wherein the section C has 1–10,000 nucleotides which sequences define a stop sequence for the RNA replicase.

7. The composition of claim 1 wherein the sections A and E comprise at least one sequence that hybridizes to a third nucleic acid to form a hybridization product which hybridization product can be detected.

8. A composition for determining the presence or absence of a target molecule comprising paired RNA molecules having a first RNA molecule and a second RNA molecule, said first RNA molecule binds a target molecule and has the following formula:

5'-A-F-B-3';

and, said second RNA binds the target and has the following formula:

5'-D-H-E-3';

wherein A is a section of the RNA molecule having 10–100,000 nucleotides which section is, with another RNA sequence, E, replicated by an RNA replicase, the letter "B" denotes a section of the RNA molecule having approximately 1 to 50000 nucleotides which section, with another sequence D, binds the target molecule under binding conditions, wherein said target is a small or large organic molecule selected from the group consisting of a peptide, protein, and derivatives thereof, the letter "D" denotes a section of the RNA molecule having approximately 1 to 50000 nucleotides which section, with another sequence B, binds the target molecule under binding conditions, wherein said target is a small or large organic molecule selected from the group consisting of a peptide, protein, and derivatives thereof, the sections B and D, in combination, comprise in total at least 10 nucleotides, the letter "F" denotes a section of the RNA molecule having has a hybridization sequence of 1–10,000 nucleotides which form a hybridization product with a section H, the letter "H" denotes a section of the RNA molecule having has a hybridization sequence of 1–10,000 nucleotides which form a hybridization product with a section F, in the absence of target, the hybridization sequences do not form a stable hybridization product, in the presence of the target, and the formation of a complex between sections B and D with the target, a hybridization product is formed that allows the RNA replicase to replicate sections A and E to form a third RNA molecule, said third RNA molecule has the following formula:

5'-E'-X-A'-3';

wherein E' is the complement to E and A' is the complement to A, the letter "X" denotes the complement of parts of the sections F and H which may be replicated, or the letter denotes the direct bond between sections E' and A' and said third RNA molecule is replicated by the RNA replicase under replicating conditions.

9. A kit for determining the presence or absence of a target molecule, said kit comprises a one or more reagents comprising a first RNA molecule for use with an RNA replicase, said first RNA molecule has the formula:

5'-A-B-C-D-E-3';

wherein A is a section of the RNA molecule having 10–100,000 nucleotides which section is, with another RNA sequence, E, replicated by an RNA replicase, the letter "B" denotes a section of the RNA molecule having approximately 1 to 50000 nucleotides which section, with another sequence D, binds the target molecule under binding conditions, wherein said target is a small or large organic molecule selected from the group consisting of a peptide, protein, and derivatives thereof, the letter "C" denotes a section of the RNA molecule having approximately 1 to 10000 nucleotides which section is capable preventing the replication of the first molecule by the RNA replicase, the letter "D" denotes a section of the RNA molecule having approximately 1 to 50000 nucleotides which section, with another sequence B, binds the target molecule under binding conditions, the sections B and D, in combination, comprise in total at least 10 nucleotides, the first RNA molecule, with sections B and D bound to target, is acted upon by the RNA replicase to form a second RNA molecule, said second RNA molecule has the following formula:

5'-E'-X-A'-3';

wherein, E' is the complement to E, and A' is the complement to A, and the letter "X" denotes the complement of parts of the sections B and D which may be replicated, or the letter denotes the direct bond between sections E' and A', and said second RNA molecule is replicated by the RNA replicase under replicating conditions, said kit for determining the presence or absence of said target molecule.

10. A kit for determining the presence or absence of a target molecule comprising paired RNA molecules said paired RNA molecules comprising a first RNA molecule and a second RNA molecule, said first RNA molecule has the formula:

5'-A-F-B-3'.

The second RNA molecule has the formula:

5'-D-H-E-3' wherein A is a section of the RNA molecule having 10–100,000 nucleotides which section is, with another RNA sequence, E, replicated by an RNA replicase, the letter "B" denotes a section of the RNA molecule having approximately 1 to 50000 nucleotides which section, with another sequence D, binds the target molecule under binding conditions, wherein said target is a small or large organic molecule selected from the group consisting of a peptide, protein, and derivatives thereof, the letter "D" denotes a section of the RNA molecule having approximately 1 to 50000 nucleotides which section, with another sequence B, binds the target molecule under binding conditions, wherein said target is a small or large organic molecule selected from the group consisting of a peptide, protein, and derivatives thereof, the sections B and D, in combination, comprise in total at least 10 nucleotides, the letter "F" denotes a section of the RNA molecule having has a hybridization sequence of 1–10,000 nucleotides which form a hybridization product with a section H, the letter "H" denotes a section of the RNA molecule having has a hybridization sequence of 1–10,000 nucleotides which form a hybridization product with a section F, in the absence of target, the hybridization sequences do not form a stable hybridization product, in the presence of the target, and the formation of a complex between sections B and D with the target, a hybridization product is formed that allows the RNA replicase to replicate sections A and E to form a third RNA molecule, said third RNA molecule has the following formula:

5'-E'-X-A'-3';

wherein E' is the complement to E and A' is the complement to A, the letter "X" denotes the complement of parts of the sections F and H which may be replicated, or the letter denotes the direct bond between sections E' and A' and said third RNA molecule is replicated by the RNA replicase under replicating conditions.

* * * * *

SEQUENCE LISTING

<160> NUMBER OF SEQ ID NOS: 15

<210> SEQ ID NO 1
<211> LENGTH: 250
<212> TYPE: RNA
<213> ORGANISM: Q-beta bacteriophage

<400> SEQUENCE: 1

```
ggggaccccc ccggaagggg gggacgaggu gcgggcaccu uguacgggag uucgaccgug      60
acgcauagca ggccucgaga ucuagagcac gggcuagcgc uuucgcgcuc ucccagguga     120
cgccucguga agaggcgcga ccucgugcgu uucggcaacg cacgagaacc gccacgcugc     180
uucgcagcgu ggcuccuucg cgcagcccgc ugcgcgaggu gacccccga  agggggguuc    240 ccgggaauuc                                                           250
```

<210> SEQ ID NO 2
<211> LENGTH: 76
<212> TYPE: RNA
<213> ORGANISM: Q-beta bacteriophage

<400> SEQUENCE: 2

```
ggggaccccc ccggaagggg gggacgaggu gcgggcaccu uguacgggag uucgaccgug      60
acgcauagca ggaauu                                                     76
```

<210> SEQ ID NO 3
<211> LENGTH: 184
<212> TYPE: RNA
<213> ORGANISM: Q-beta bacteriophage

```
<400> SEQUENCE: 3 ggggacccccc cgggccucga gaucuagagc acgggcuagc gcuuucgcgc ucucccagug    60
acgccucgug aagaggcgcg accuucgugc guuucggcaa cgcacgagaa ccgccacgcu   120
gcuucgcagc guggcuccuu cgcgcagccc gcugcgcgag ugaccccccc gaagggggu    180 uccc                                                                184

<210> SEQ ID NO 4
<211> LENGTH: 80
<212> TYPE: RNA
<213> ORGANISM: Artificial Sequence
<220> FEATURE:
<223> OTHER INFORMATION: Description of Artificial Sequence:DERIVED FROM
      REACTION PRODUCT OF Q-BETA REPLICASE

<400> SEQUENCE: 4 ggggguuucca accggaauuu gagggaugcc uaggcauccc ccgugcguuc cuuuacgagg    60
gauugucgac ucagucgac                                                 80

<210> SEQ ID NO 5
<211> LENGTH: 75
<212> TYPE: RNA
<213> ORGANISM: Artificial Sequence
<220> FEATURE:
<223> OTHER INFORMATION: Description of Artificial Sequence:DERIVED FROM
      REACTION PRODUCT OF Q-BETA REPLICASE

<400> SEQUENCE: 5
gguaccugag ggaugccuag gcaucccccgc gcgccgguuu cggaccucca gugcguguua    60
ccgcacuguc gaccc                                                     75

<210> SEQ ID NO 6
<211> LENGTH: 26
<212> TYPE: RNA
<213> ORGANISM: Artificial Sequence
<220> FEATURE:
<223> OTHER INFORMATION: Description of Artificial Sequence:
      APTOMER FOR ATP

<400> SEQUENCE: 6
aguugggaag aaacuguggg acuucg                                          26

<210> SEQ ID NO 7
<211> LENGTH: 12
<212> TYPE: RNA
<213> ORGANISM: Artificial Sequence
<220> FEATURE:
<223> OTHER INFORMATION: Description of Artificial Sequence:
      APTOMER FOR ATP

<400> SEQUENCE: 7
gucccagcaa cu                                                         12

<210> SEQ ID NO 8
<211> LENGTH: 15
<212> TYPE: RNA
<213> ORGANISM: Artificial Sequence
<220> FEATURE:
<223> OTHER INFORMATION: Description of Artificial Sequence:SARCIN
      RECOGNITION

<400> SEQUENCE: 8
auguacgaga ggacc                                                      15
```

<210> SEQ ID NO 9
<211> LENGTH: 70
<212> TYPE: RNA
<213> ORGANISM: Artificial Sequence
<220> FEATURE:
<223> OTHER INFORMATION: Description of Artificial Sequence:
      APTOMER FOR ATP

<400> SEQUENCE: 9
cgagggggga agaaacgggc accgggccag caaccccca accccgacac cggaagccac      60
ggcggggagc                                                            70

<210> SEQ ID NO 10
<211> LENGTH: 102
<212> TYPE: RNA
<213> ORGANISM: Artificial Sequence
<220> FEATURE:
<223> OTHER INFORMATION: Description of Artificial Sequence:COMBINED MDV-1
      AND ATP APTOMER

<400> SEQUENCE: 10
ggggaccccc ccggaagggg gggacgaggu gcgggcaccu uguacgggag uucgaccgug      60
acgcauagca ggaguuggga agaaacugug ggacuucgaa uu                       102

<210> SEQ ID NO 11
<211> LENGTH: 196
<212> TYPE: RNA
<213> ORGANISM: Artificial Sequence
<220> FEATURE:
<223> OTHER INFORMATION: Description of Artificial Sequence:
      COMBINED MDV-1 AND ATP APTOMER

<400> SEQUENCE: 11
ggggaccccc cgggguccca gcaacuccuc gagaucuaga gcacgggcua gcgcuuucgc      60
gcucucccag ugacgccucg ugaagaggcg cgaccuucgu gcguuucggc aacgcacgag    120
aaccgccacg cugcuucgca gcguggcucc uucgcgcagc ccgcugcgcg aggugaccc     180 ccgaaggggg guuccc                                                    196

<210> SEQ ID NO 12
<211> LENGTH: 157
<212> TYPE: RNA
<213> ORGANISM: Artificial Sequence
<220> FEATURE:
<223> OTHER INFORMATION: Description of Artificial Sequence:RQT RNA WITH
      CLONING SITES

<400> SEQUENCE: 12 ggggguuucca accggaauuu gagggaugcc uaggcauccc ccgugcgucc cuuuacgagg    60
gauugucgac ucuagaggau ccgguaccug agggaugccu aggcaucccc gcgcgccggu   120
uucggaccuc cagugcgugu uaccgcacug ucgaccc                             157

<210> SEQ ID NO 13
<211> LENGTH: 102
<212> TYPE: RNA
<213> ORGANISM: Artificial Sequence
<220> FEATURE:
<223> OTHER INFORMATION: Description of Artificial Sequence:RQT WITH REV
      AND SARCIN RECOGNITION SITES

<400> SEQUENCE: 13 ggggguuucca accggaauuu gagggaugcc uaggcauccc ccgugcgucc cuuuacgagg    60
gauugucgac ucuagucgac gucugggcga aaaauguacg ag                       102

<210> SEQ ID NO 14
<211> LENGTH: 95
<212> TYPE: RNA
<213> ORGANISM: Artificial Sequence
<220> FEATURE:
<223> OTHER INFORMATION: Description of Artificial Sequence:RQT WITH REV
      AND SARCIN RECOGNITION SITES

<400> SEQUENCE: 14
aggaccuuuu cgguacagac gguaccugag ggaugccuag gcaucccgc gcgccgguuu      60 cggaccucca gugcguguua ccgcacuguc gaccc                               95

<210> SEQ ID NO 15
<211> LENGTH: 197
<212> TYPE: RNA
<213> ORGANISM: Artificial Sequence
<220> FEATURE:
<223> OTHER INFORMATION: Description of Artificial Sequence:
      RQT WITH SARCIN AND REV RECOGNITION SITES

<400> SEQUENCE: 15
gggguuucca accggaauuu gagggaugcc uaggcauccc ccgugcgucc cuuuacgagg     60
gauugucgac ucuagucgac gucugggcga aaaauguacg agaggaccuu uucgguacag    120
acgguaccug agggaugccu aggcauccccc gcgcgccggu uucggaccuc cagugcgugu   180
uaccgcacug ucgaccc                                                  197